United States Patent [19]

Green

[11] Patent Number: 5,361,522
[45] Date of Patent: Nov. 8, 1994

[54] AIR FRESHENER PICTURE FRAME

[76] Inventor: Dennis E. Green, 102 Falcon Hills Dr., Highlands Ranch, Colo. 80126

[21] Appl. No.: 188,483

[22] Filed: Jan. 28, 1994

[51] Int. Cl.⁵ ............................................. G09F 1/12
[52] U.S. Cl. ..................................... 40/152.1; 40/152; 239/58
[58] Field of Search ............... 40/152, 152.1; 239/57, 239/58, 59, 60

[56]  References Cited

U.S. PATENT DOCUMENTS

| | | | |
|---|---|---|---|
| D. 269,902 | 7/1983 | Edwards | D23/150 |
| 1,692,999 | 11/1928 | Siegal | 40/124.1 |
| 2,550,954 | 5/1951 | Benedict | 239/57 |
| 2,577,320 | 12/1951 | Fenyo | 41/14 |
| 3,540,146 | 11/1970 | Watkins | 40/152.1 |
| 4,229,892 | 10/1980 | Hueter et al. | 40/152.1 |
| 4,432,152 | 2/1984 | Daenen | 40/152.1 |
| 4,814,212 | 3/1989 | Spector | 428/14 |
| 4,993,177 | 2/1991 | Hudson | 40/152.1 |
| 5,174,054 | 12/1992 | Politi | 40/152 |
| 5,304,358 | 4/1994 | Hoyt et al. | 239/56 X |

FOREIGN PATENT DOCUMENTS

| | | | |
|---|---|---|---|
| 66012 | 4/1956 | France | 239/57 |
| 560143 | 3/1975 | Switzerland | 239/59 |

*Primary Examiner*—Kenneth J. Dorner
*Assistant Examiner*—Cassandra Davis
*Attorney, Agent, or Firm*—Dorr, Carson, Sloan & Peterson

[57]  ABSTRACT

A combination air freshener and picture frame includes a front frame to receive a picture and a removable back insert that can be attached to the frame to retain the picture against the front face of the picture frame. The front frame has a central opening for viewing the picture in the frame. An enclosure adjacent to the rear portion of the frame contains an air freshener material. The enclosure has openings to allow diffusion of the air freshener scent into the ambient atmosphere. A removable cap is attached to cover the openings in the enclosure. A number of props are pivotally connected to the back side of the rear portion of the frame and to the removable cap for selectively supporting the frame in any of a number of possible orientations.

18 Claims, 6 Drawing Sheets

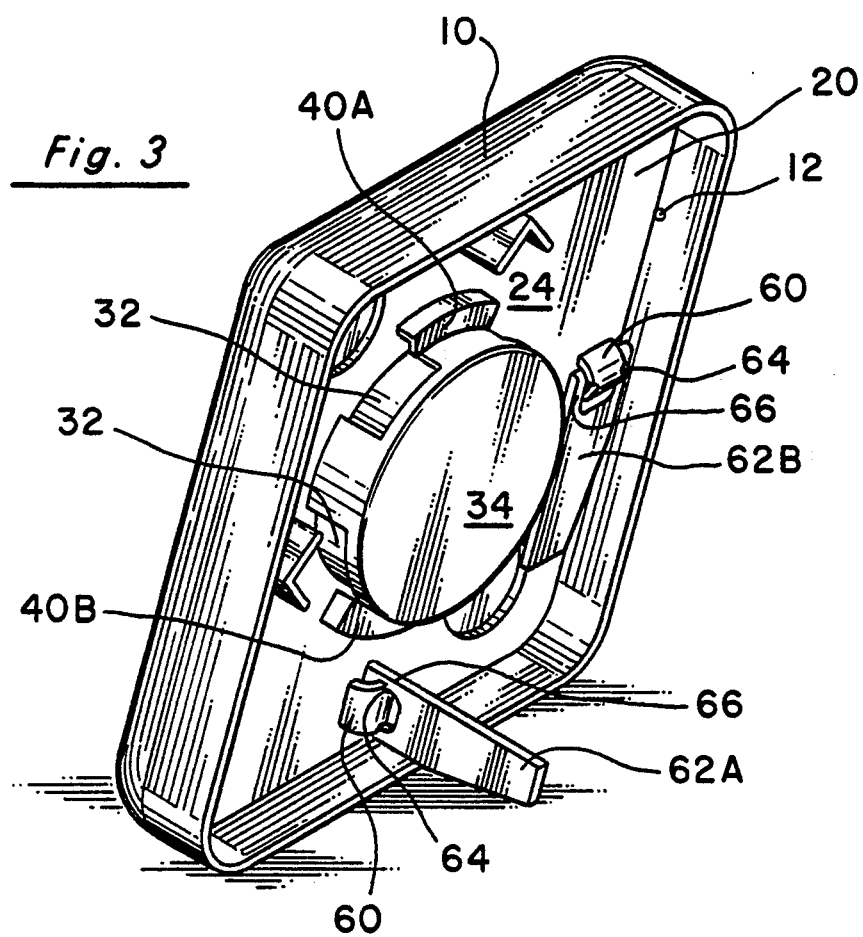
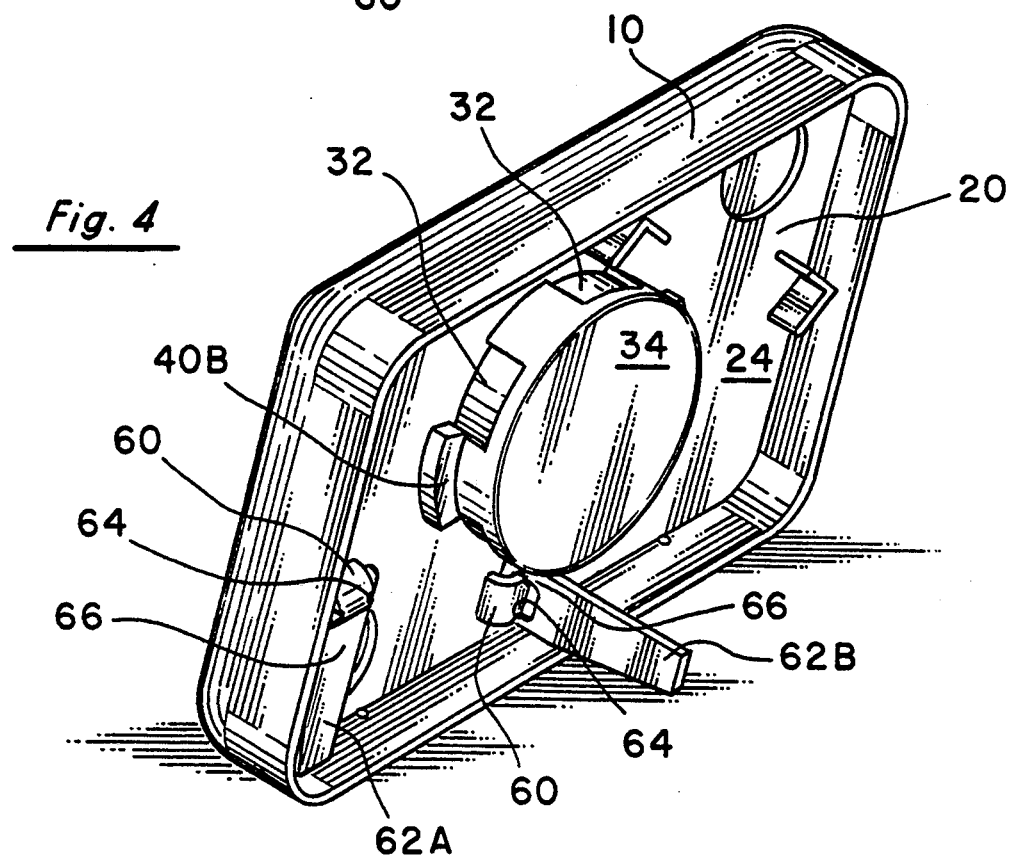

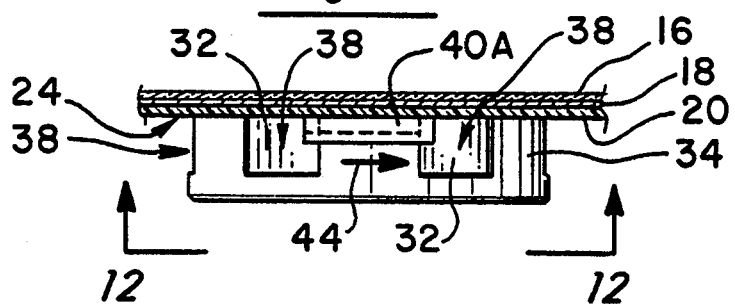
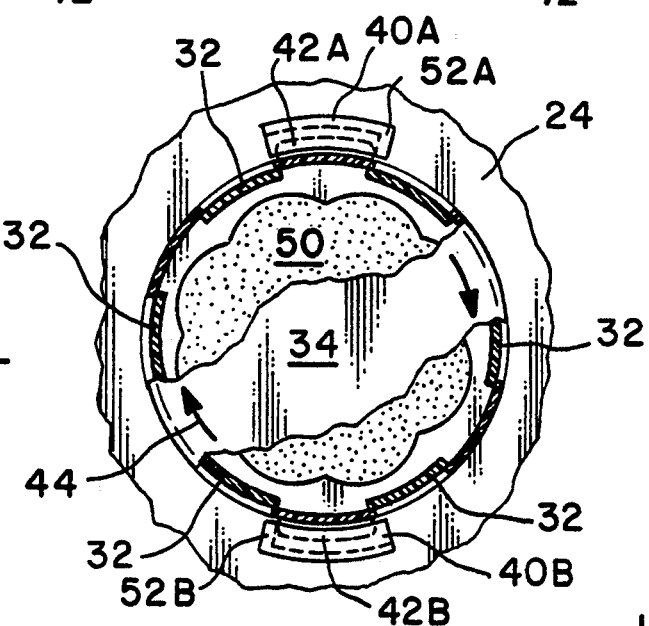
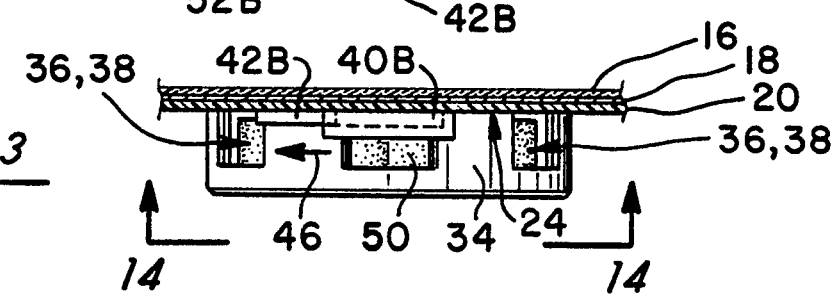
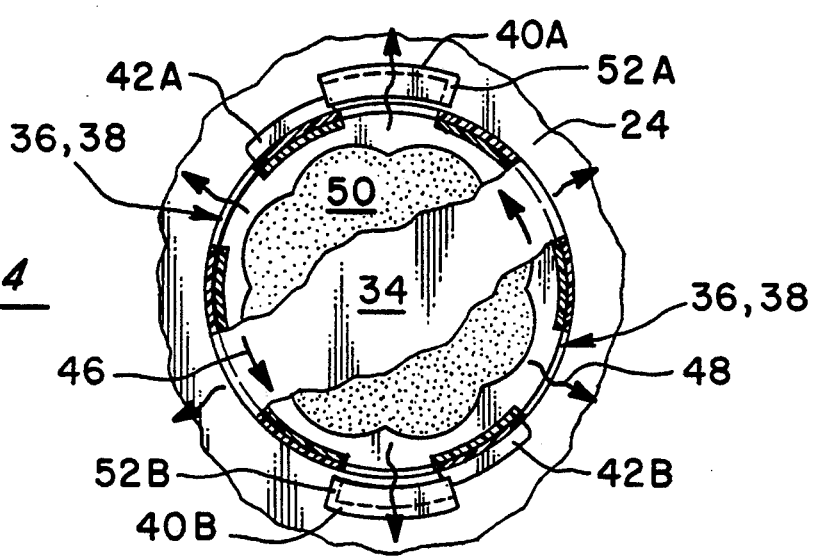

AIR FRESHENER PICTURE FRAME

BACKGROUND OF THE INVENTION

1. Field of the Invention

The present invention relates generally to the field of air fresheners. More specifically, the present invention discloses an air freshener combined with a back-loading, self-supporting picture frame.

2. Statement of the Problem

Ideally, an air freshener should meet a number of design criteria. Foremost, of course, is the requirement that the air freshener must effectively dispense a desired fragrance over an extended period. Second, the air freshener either should be aesthetically unobtrusive or, preferably, should be aesthetically pleasing. Several past inventors have recognized that this second criterion can be addressed by incorporating an air freshener as part of a picture frame. This allows the air freshener to be unobtrusively hidden behind an aesthetically pleasing frame holding artwork or a photograph. In most of these combinations, the user can select the artwork or photograph to be displayed in the frame.

Nonetheless, several potential problems exist with these prior art devices. The user should be able to easily replace the picture held in the frame. In particular, the user should not have to risk spilling or coming into contact with the air freshener material while replacing the picture. The frame should be readily supported in either a vertical or horizontal position. Finally, the air freshener should be kept sealed until it is ready to be used by the customer, and preferably should have the ability to be resealed at any time by the customer to conserve the fragrance.

As previously mentioned, a number of air fresheners combined with picture displays have been invented in the past. In addition, a variety of self-supporting back-loading picture frames have been previously invented. These include the following:

| Inventor | U.S. Pat. No. | Issue Date |
| --- | --- | --- |
| Siegal | 1,692,999 | Nov. 27, 1928 |
| Fenyo | 2,577,320 | Dec. 4, 1951 |
| Watkins | 3,540,146 | Nov. 17, 1970 |
| Hueter et al. | 4,229,892 | Oct. 28, 1980 |
| Edwards | D.269,902 | July 26, 1983 |
| Daenen | 4,432,152 | Feb. 21, 1984 |
| Spector | 4,814,212 | Mar. 21, 1989 |
| Hudson | 4,993,177 | Feb. 19, 1991 |
| Politi | 5,174,054 | Dec. 29, 1992 |

Siegal discloses a two-part picture frame in which spring devices 8 are used to hold a front section inside a back section.

Fenyo discloses a picture frame 15 having a recess 23 to accommodate a perfumed wick 24. As shown in FIGS. 9 and 10, the recess 23 has a lid with apertures 28 to allow the odor to be emitted.

Watkins discloses a frame having an easel back 15 with a swing leg 16 to prop the frame upright.

Hueter et al. disclose a display device having a frame holder 14, a support member 32, and an adapter 22 attached to the back panel 12 of the frame holder. The frame holder can be hung in either orientation using the adapter. In addition, the frame holder can be made freestanding by engaging the support member 32 to the adapter 22.

Edwards discloses a combined air freshener and photo frame. As shown in FIGS. 4 and 5, the upper edge of the frame can be slid upward to expose the air freshener contained within.

Daenen discloses a modular picture frame 10 with a hanger/holder 16 that can be used interchangeably to support the frame as shown in FIGS. 1–4, 11, and 12; to hang the frame as shown in FIG. 6; or to attach several frames together as shown in FIG. 10. In addition, the assembly includes a window 14 that press-fits into engagement with the front surface of the frame.

Spector discloses an automobile air freshener having a frame to hold artwork. The rear surface is coated with a pressure-sensitive adhesive to attach to the car window. The front of the frame is impregnated with a volatile fragrance that is slowly released into the atmosphere.

Hudson discloses a picture frame with an air freshener pad 27 positioned behind the rear surface of the frame. A bracket or pocket 32 holds one edge of the air freshener pad 27. A bridge 33 extends across the midsection of the pad 27 to hold it in place against the rear surface of the frame. It appears that the device would have to be disassembled from the rear in order to replace the photograph. This would probably require the user to handle the exposed air freshener pad attached to the rear of the frame.

Politi discloses a back-loading picture frame with a rear backing member 13 that fits into a front frame 11, holding a picture therebetween. A rear strut 41 is swingably attached to the backing member 13 by at least one of two sets of hinge lugs 45.

3. Solution to the Problem

None of the prior art references uncovered in the search show a combination air freshener and picture frame having the structure of the present invention that meets the design criteria discussed above. In particular, the present invention provides an aesthetically pleasing air freshener with a back-loading frame that permits easy replacement of the picture without exposing the user to the air freshener material. The removable cap in the present invention serves to seal the air freshener enclosure when not in use and to adjust the amount of fragrance that is released. The props of the present invention support the frame in a vertical or horizontal orientation without requiring effort on the part of the user to move the prop from one hinge to another, or to attach the support to the back of the frame.

SUMMARY OF THE INVENTION

This invention provides a combination air freshener and picture frame. The picture frame has a front frame to receive a picture and a removable back insert that can be attached to the frame to retain the picture against the front face of the picture frame. The front frame has a central opening for viewing the picture in the frame. An enclosure adjacent to the rear portion of the frame contains an air freshener material. The enclosure has openings to allow diffusion of the air freshener scent into the ambient atmosphere. A removable cap can be attached to cover the openings in the enclosure. A number of props are pivotally connected to the back side of the rear portion of the frame for selectively supporting the frame in any of a corresponding number of possible orientations.

A primary object of the present invention is to provide a combination air freshener and picture frame in which the picture can be easily inserted into the frame from the back without the risk of contact with the air freshener.

Another object of the present invention is to provide a combination air freshener and picture frame that can be readily supported by a prop in either a vertical or horizontal orientation.

Yet another object of the present invention is to provide a combination air freshener and picture frame in which the user can control the amount of fragrance released and seal the air freshener enclosure when it is not in use.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 3 is a rear perspective view of the present invention in the vertical orientation.

FIG. 4 is a rear perspective view of the present invention in the horizontal orientation.

FIG. 11 is a top elevational view of the enclosure showing the cap with the vents closed.

FIG. 12 is a rear elevational view in partial cross-section of the enclosure showing the cap with the vents closed.

FIG. 13 is a top elevational view of the enclosure showing the vents open.

FIG. 14 is a rear elevational view in partial cross-section of the enclosure showing the vents open.

DETAILED DESCRIPTION OF THE INVENTION

Figure 1:
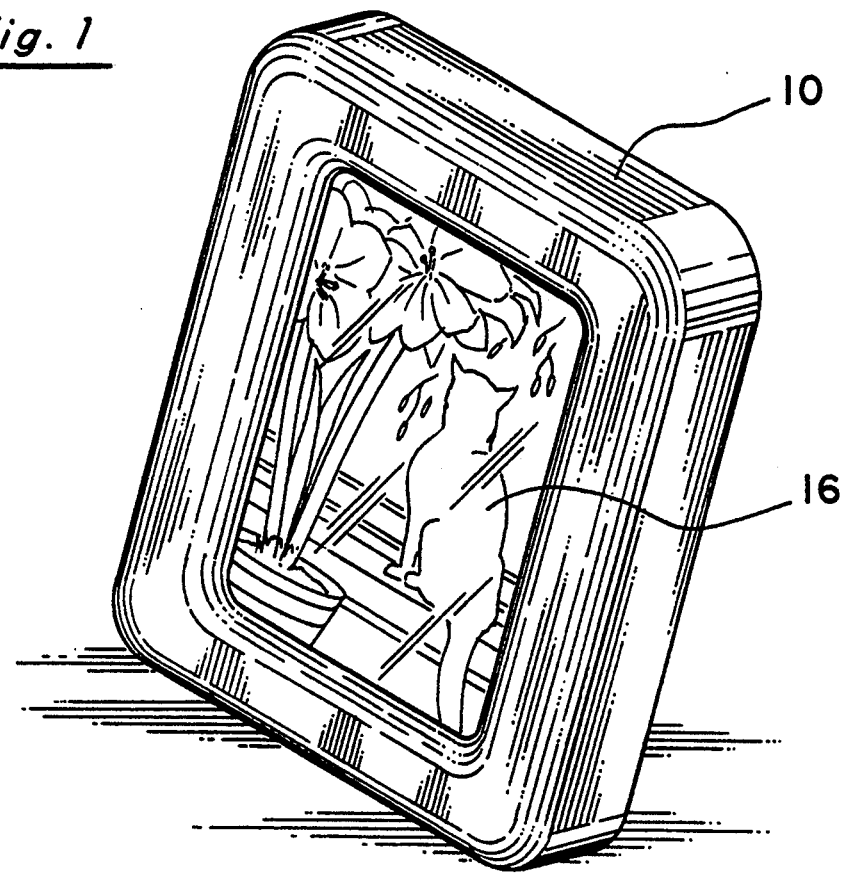
FIG. 1 is a front perspective view of the present invention in the vertical orientation.
Figure 2:
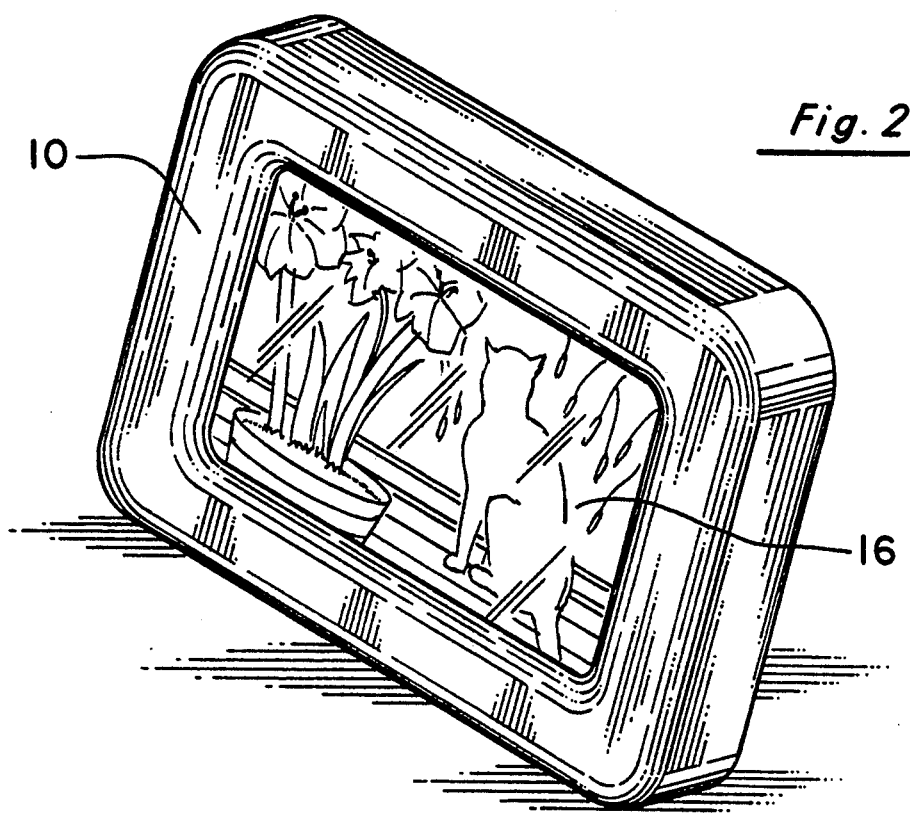
FIG. 2 is a front perspective view of the present invention in the horizontal orientation.
Figure 5:
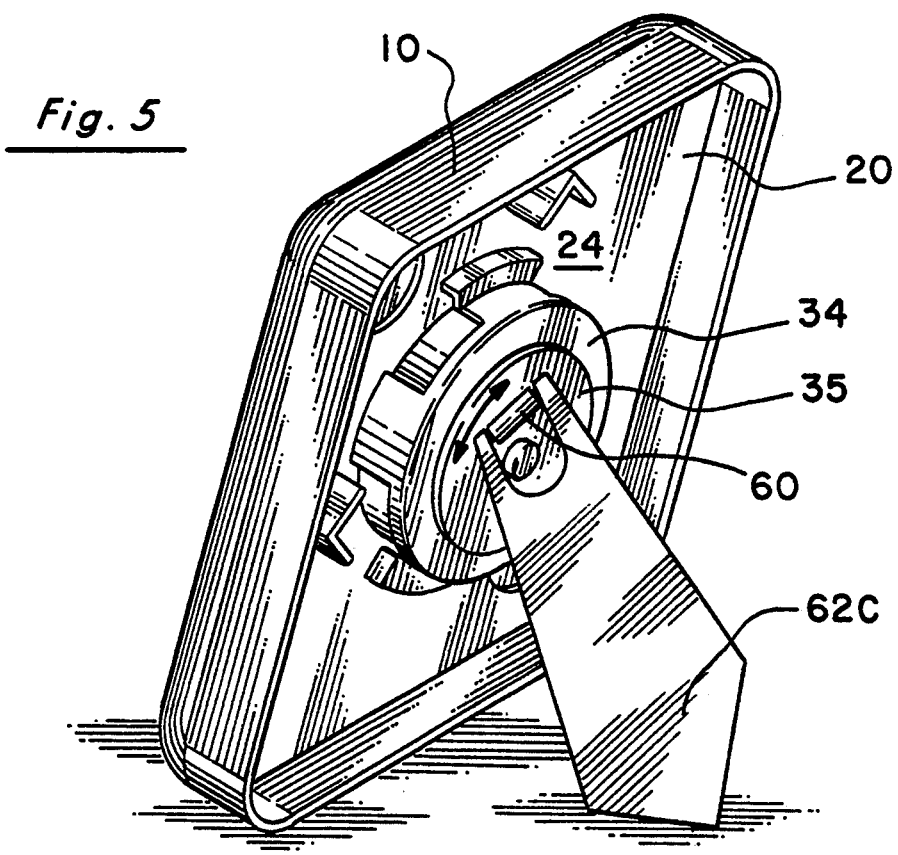
FIG. 5 is a rear perspective view of the present invention in the vertical orientation showing an alternative prop.
Figure 6:
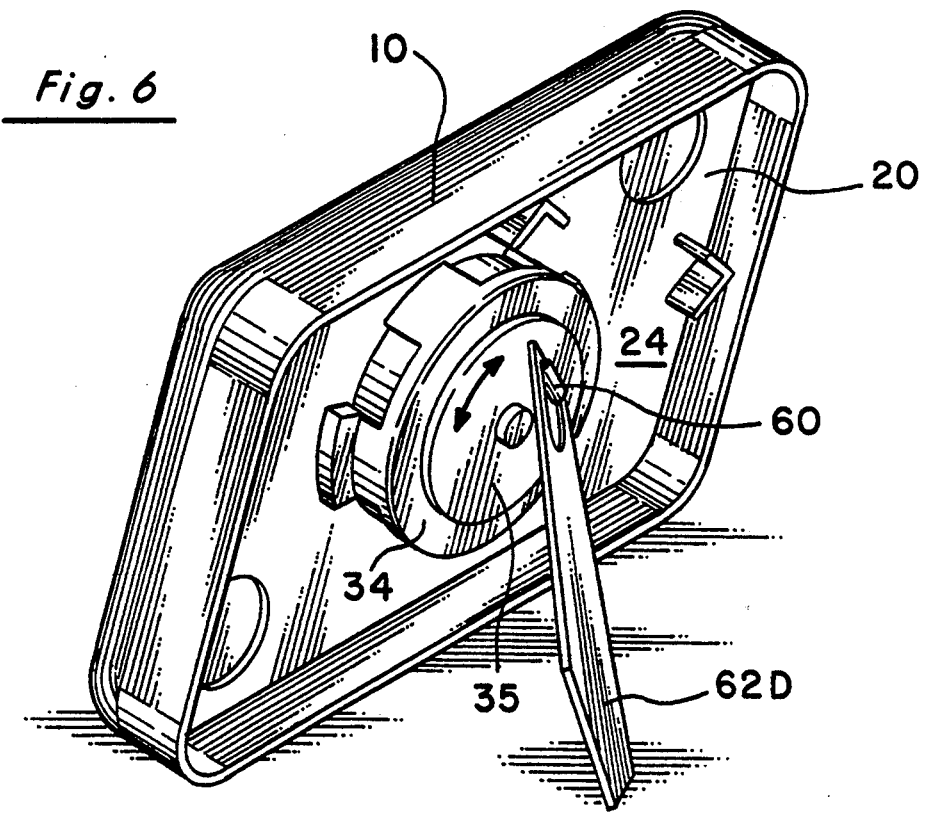
FIG. 6 is a rear perspective view of the present invention in the horizontal orientation showing an alternative prop.

FIGS. 1 and 2 show a front perspective view and FIGS. 3-6 show a rear perspective view of the present invention in the vertical (FIGS. 1, 3, and 5) and horizontal (FIGS. 2, 4, and 6) orientations. In FIG. 3, prop 62a is extended to support the frame. In FIG. 4, prop 62b is extended to support the frame. In FIG. 5, prop 62c is extended to support the frame. In FIG. 6, prop 62d is extended to support the frame.

Figure 7:
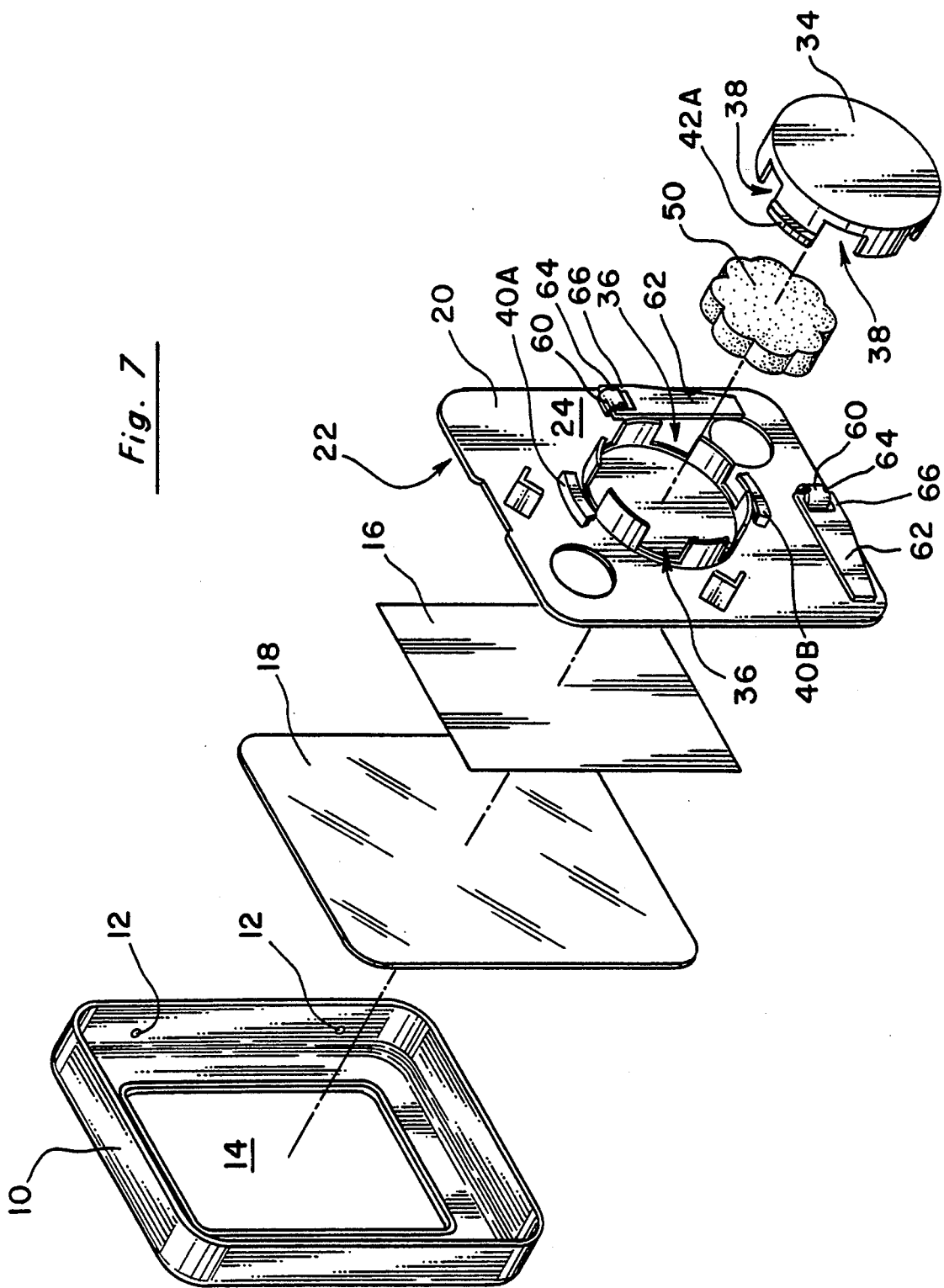
FIG. 7 is an exploded rear perspective view of the present invention.
Figures 8, 9:
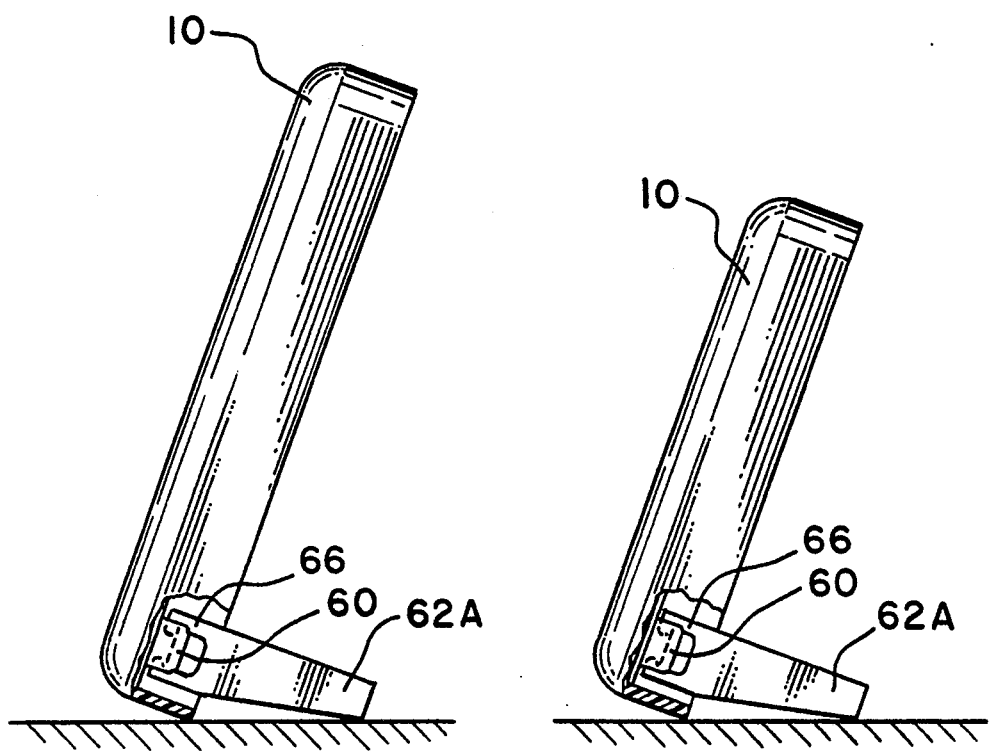
FIG. 8 is a side view in partial cross-section of the present invention in the vertical orientation.
FIG. 9 is a side view in partial cross-section of the present invention in the horizontal orientation.

Turning to FIG. 7, a clear sheet 18 is first placed within the front display member 10 from the back so that the clear sheet 18 abuts the front opening 14. The artwork 16 that the user desires to show is then placed flat against the clear sheet 18 so that the artwork 16 faces out and can be viewed through the front opening 14. A back panel 20 is fitted within the front display member 10 so that the artwork 16 is sandwiched between the clear sheet 18 and the front side 22 of the back panel 20.

The back panel 20 is held within the front display member 10 by several retaining members 12. In the preferred embodiment, these retaining members 12 are small bumps extending inwardly from the rear, inside surfaces of the front display member 10, as shown in FIG. 7. The dimensions of the back panel 20 are slightly larger than the dimensions of the clear sheet 18. Alternatively, other types of fasteners could be substituted for the retaining members 12, such as clips, Velcro, magnets, or matching sets of indentations and protrusions on the back panel and frame.

Figure 10:
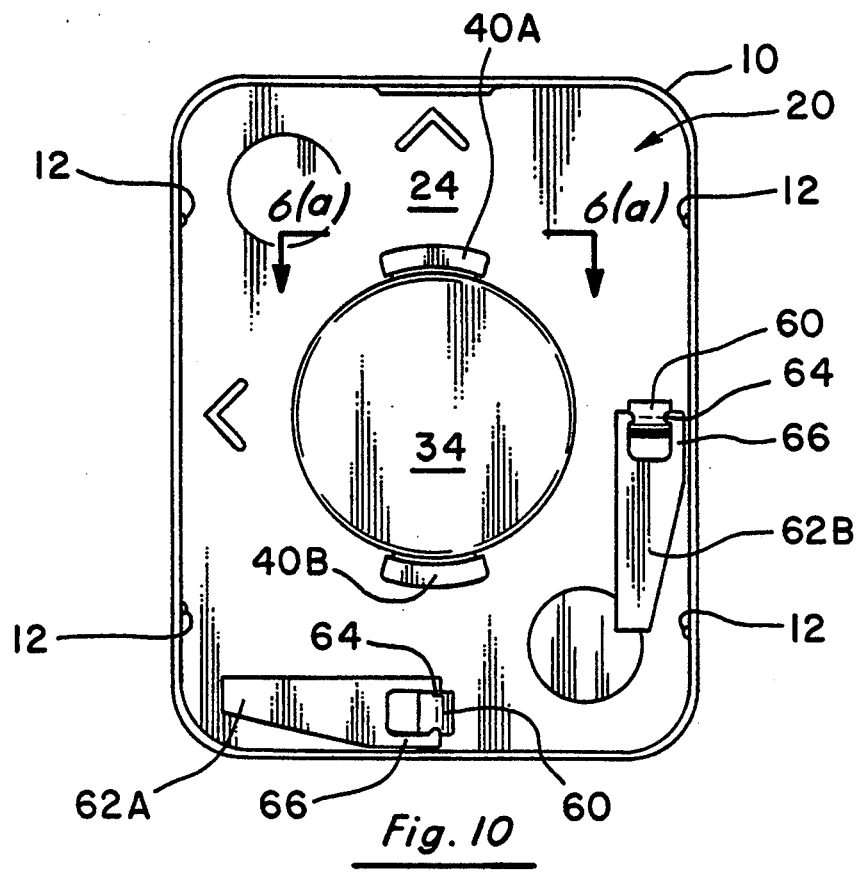
FIG. 10 is a rear elevational view of the present invention.

Air freshener material 50 is contained within an enclosure attached to the back side 24 of the back panel 20 as shown in FIGS. 7 and 10. The enclosure is formed from two sections 32 and 34 in the preferred embodiment of the invention. The first section 32 consists of a circular dam having a multitude of vents 36. The first section 32 is an integral part of the back panel 20. The second section of the enclosure is a circular cap 34 that fits tightly over the first section 32 of the enclosure. This circular cap 34 also has vents 38 cut into its sidewalls. These vents 38 have dimensions similar to those of the vents 36 of the first section 32. Two lips 42a and 42b extend out from the sidewalls of the circular cap 34, 180 degrees apart. Two brackets 40a and 40b are attached to the back side 24 of the back panel 20 just outside of and at opposite sides of the first section 32 of the enclosure. Lip 42a fits into bracket 40a and lip 42b fits into bracket 40b when circular cap 34 is rotated clockwise upon the first section 32 of the enclosure as shown by the arrows 44 in FIG. 12. A stop 52a, 52b at the end of each respective bracket 40a, 40b prevents the lips 42a, 42b from rotating out of the brackets 40a, 40b so that at the completion of the clockwise rotation, all the vents 36, 38 are sealed, preventing the release of fragrance from the air freshener material 50. When the user desires to release the air freshener scent, the user rotates the circular cap 34 counter-clockwise as shown by arrows 46 in FIG. 14, thus opening the vents 36, 38 and releasing the scent 48.

At least two U-shaped extensions 60 are attached to adjacent sides of the back side 24 of the back panel 20. At least two props 62a and 62b are pivotally connected to the U-shaped extensions by corresponding openings 66 in the ends of the props 62a, 62b. In the preferred embodiment, these openings 66 are roughly C-shaped and have a diameter that is slightly less than the width of the U-shaped extension 60 that the C-shaped end 66 is wrapped around. When prop 62a, 62b is pivoted, C-shaped end 66 will pop into notches 64 cut into U-shaped extension 60, as shown by FIGS. 3 and 4, preventing any further pivoting by prop 62a, 62b. By choosing the appropriate prop 62a or 62b, the user can selectively support the present invention in either a vertical or a horizontal orientation as shown in FIGS. 1-4, 8-9. It should be expressly understood that the extensions 60 could be readily changed from U-shaped to V-shaped, an oval, or a rectangular cross-section without significantly altering the functionality of the device. Similarly, the ends 66 of the props 62a, 62b could be readily changed to other equivalent shapes. Alternatively, a single prop might be similarly attached to either the back side 24 or the circular cap 34 of the enclosure as shown in FIGS. 5 and 6. This prop would function to support the combination air freshener and picture frame in either the vertical or horizontal position. A counter-rotating disk enables the single prop to be used when the circular cap 34 is rotated to open the air freshener enclosure.

I claim:

1. A combination air freshener and picture frame comprising:
   a front display member having retaining members;
   a back panel fitting within said front display member and removably engaged by said retaining members;
   air freshener material for emitting a scent;
   an enclosure attached to said back panel, said enclosure containing said air freshener material;
   means for controlling the release of said scent; and
   at least one prop pivotally connected relative to said back panel for selectively supporting said combination air freshener and picture frame in a plurality of possible orientations.

2. The combination air freshener and picture frame of claim 1, wherein said front display member has an opening through which to view artwork.

3. The combination air freshener and picture frame of claim 1, wherein said props are placed along adjacent sides edges of said back panel so as to selectively support said back panel along at least one of side edge of said frame.

4. The combination air freshener and picture frame of claim 1, wherein at least one prop is placed on said back panel so as to support said back panel along at least one of side edge of said frame.

5. The combination air freshener and picture frame of claim 4, wherein said prop is attached to said enclosure.

6. A combination air freshener and picture frame comprising:
   a front display member having an opening therein through which to view artwork;
   a back panel having a front side and a back side, said back panel fitting within said front display member;
   air freshener material for emitting a scent;
   an enclosure attached to said back side of said back panel, said enclosure containing said air freshener material;
   means for controlling the release of said scent; and
   at least one prop pivotally connected relative to said back side of said back panel for selectively supporting said combination air freshener and picture frame in a plurality of possible orientations.

7. The combination air freshener and picture frame of claim 6, wherein said front display member has retaining members for removably engaging said back panel.

8. The combination air freshener and picture frame of claim 6, further comprising a clear sheet fitting within said front display member between said opening and said back panel.

9. The combination air freshener and picture frame of claim 6, wherein said enclosure has a first section and a second section, said first section being an integral part of said back panel and said second section removably capping said first section.

10. The combination air freshener and picture frame of claim 9, wherein said second section of said enclosure comprises a circular cap.

11. The combination air freshener and picture frame of claim 9, wherein said first and second sections of said enclosure have vents for controllably releasing said scent.

12. The combination air freshener and picture frame of claim 6, wherein said props are placed along adjacent sides edges of said back side of said back panel so as to selectively support said back panel along at least one side edge of said frame.

13. The combination air freshener and picture frame of claim 6, wherein at least one prop is placed on said back panel so as to support said frame along at least one of side edges of said frame.

14. The combination air freshener and picture frame of claim 13, wherein said prop is attached to said enclosure.

15. A combination air freshener and picture frame comprising:
   a front display member having an opening therein through which to view artwork, said front display member also having retaining members;
   a back panel having a front side and a back side, said back panel retained within said front display member by said retaining members;
   air freshener material for emitting a scent;
   an enclosure attached to said back side of said back panel, said enclosure containing said air freshener material;
   means for controlling the release of said scent, said means comprising a rotatable cap having vents therein rotating relative to said enclosure;
   means to support said combination air freshener and picture frame in a plurality of orientations, said support means comprising:
   a first U-shaped extension secured near a first side of said back side of said back panel;
   a first prop pivotally attached to said first U-shaped extension;
   a second U-shaped extension secured near a second side of said back side of said back panel; and
   a second prop pivotally attached to said second U-shaped extension.

16. The combination air freshener and picture frame of claim 15, further comprising a clear sheet fitting within said front display member between said opening and said back panel.

17. The combination air freshener and picture frame of claim 15, wherein said first and second U-shaped extensions are placed on adjacent sides edges of said back side of said back panel so that said back panel is supported either along a first of said side edge by said first prop or along a second of said side edges by a second prop.

18. The combination air freshener and picture frame of claim 15, wherein said first and second U-shaped extensions have a notch therein for stabilizing said first and second props.

* * * * *